(12) United States Patent
Yamaji et al.

(10) Patent No.: US 9,279,787 B2
(45) Date of Patent: Mar. 8, 2016

(54) CRANKSHAFT FLAW DETECTION DEVICE

(71) Applicant: Kobe Steel, Ltd., Kobe-shi (JP)

(72) Inventors: Tetsuo Yamaji, Takasago (JP); Yasuhiro Wasa, Kobe (JP); Akira Okamoto, Kobe (JP); Norio Suzuki, Takasago (JP); Hideyuki Chikuri, Takasago (JP)

(73) Assignee: Kobe Steel, Ltd., Kobe-shi (JP)

( * ) Notice: Subject to any disclaimer, the term of this patent is extended or adjusted under 35 U.S.C. 154(b) by 0 days.

(21) Appl. No.: 14/418,290

(22) PCT Filed: Aug. 22, 2013

(86) PCT No.: PCT/JP2013/004963
§ 371 (c)(1),
(2) Date: Jan. 29, 2015

(87) PCT Pub. No.: WO2014/038149
PCT Pub. Date: Mar. 13, 2014

(65) Prior Publication Data
US 2015/0300994 A1    Oct. 22, 2015

(30) Foreign Application Priority Data

Sep. 6, 2012 (JP) ................................ 2012-196028

(51) Int. Cl.
*G01N 29/04* (2006.01)
*G01N 29/265* (2006.01)
*G01N 29/22* (2006.01)

(52) U.S. Cl.
CPC .............. *G01N 29/265* (2013.01); *G01N 29/04* (2013.01); *G01N 29/225* (2013.01)

(58) Field of Classification Search
CPC ..... G01N 29/04; G01N 29/26; G01N 29/225; G01N 29/265; G01N 29/223; G01N 29/28

USPC ........... 73/618, 622, 625, 628, 637, 640, 644, 73/632, 641, 633
See application file for complete search history.

(56) References Cited

U.S. PATENT DOCUMENTS 3,913,388 A * 10/1975 Berner ................. G01N 29/223
                                                                  73/634
4,783,998 A * 11/1988 Sander ...................... G01P 3/56
                                                                  73/660

(Continued)

FOREIGN PATENT DOCUMENTS

JP   51 63678    6/1976
JP   54 114289   9/1979

(Continued)

OTHER PUBLICATIONS

Written Opinion of the International Searching Authority Issued Oct. 22, 2013 in PCT/JP13/004963 Filed Aug. 22, 2013.

(Continued)

*Primary Examiner* — Helen Kwok
(74) *Attorney, Agent, or Firm* — Oblon, McClelland, Maier & Neustadt, L.L.P.

(57) ABSTRACT

A crankshaft flaw detection device (1) used for detecting flaws in the crank pin, web, and fillet section of a crankshaft comprises: a pair of shaft flaw detection heads (2, 3) configured so as to be capable of sandwiching the crank pin (C2) therebetween, and having a first probe (2*b*) capable of detecting flaws on the shaft surface of the crank pin (C2) or a second probe (3*b*) capable of detecting flaws in a fillet section at the base of the shaft; and a perpendicular surface flaw detection head (4) configured so as to be capable of coming in contact with the crank pin (C2) and having a third probe (4*b*) capable of detecting flaws in the side surface of the web (C3). The crankshaft flaw detection device (1) is characterized by the perpendicular surface flaw detection head (4) and the pair of shaft flaw detection heads (2, 3) being movable within the perpendicular surface

6 Claims, 3 Drawing Sheets

(56) References Cited

U.S. PATENT DOCUMENTS 6,161,436 A * 12/2000 McLean, Jr. ......... G01N 29/223
                                                        73/632
2005/0223809 A1   10/2005  Murphy et al.

FOREIGN PATENT DOCUMENTS

| JP | 3 63857 | 6/1991 |
| JP | 9 264877 | 10/1997 |
| JP | 10 142104 | 5/1998 |
| JP | 2004-361353 A | 12/2004 |
| JP | 2005 300544 | 10/2005 |
| JP | 2006 212715 | 8/2006 |
| JP | 2008 209148 | 9/2008 |
| JP | 2009 82994 | 4/2009 |

OTHER PUBLICATIONS

International Search Report Issued Oct. 22, 2013 in PCT/JP13/004963 Filed Aug. 22, 2013.

* cited by examiner

US 9,279,787 B2

CRANKSHAFT FLAW DETECTION DEVICE

TECHNICAL FIELD

The present invention relates to a crankshaft flaw detection device.

BACKGROUND ART

A crankshaft, which is a component of an engine, includes journal sections, crank pins, and webs each for coupling the journal section and the crank pin to each other. When the crankshaft is delivered, a quality inspection (ultrasonic examination) is required for these sections. The quality inspection is generally carried out through manual scanning of probes. However, the manual inspection takes a very much time, and thus requires many man-hours for a large crankshaft having a large diameter or many numbers of pins.

On the other hand, a system for automating a quality inspection for a cylindrical shaft used for turbine and the like without the crank pin sections (eccentric sections) is known as disclosed in Patent Literature 1. This system is a system in which a probe is brought in contact with a surface of the shaft, and peripheral scanning for flaw detection is carried out while the shaft is being rotated. The surface flaw detection for the journal section can be automatically carried out by rotating the crankshaft in this system. However, the surface flaw detection cannot be carried out on the crank pin which revolves eccentrically in this system. In other words, the crank pin cannot be rotated about the axial center of the crank pin, and the system cannot be applied to scanning for the flaw detection other than that for the journal sections.

CITATION LIST

Patent Document

Patent Document 1: JP2005-300544 A

SUMMARY OF THE INVENTION

It is an object of the present invention to provide a crankshaft flaw detection device capable of automating flaw detections on crank pins, journal sections, webs, and fillet sections, thereby greatly decreasing a scanning for flaw detection time.

A crankshaft flaw detection device according to one aspect of the present invention for detecting a flaw of a crankshaft including at least two journal sections arranged on the same axial center, a crank pin arranged in an eccentric state between the two journal sections adjacent to each other, and a web in a plate shape for coupling the crank pin and the journal section adjacent to each other to each other, in a state where the journal sections are disposed so as to be approximately horizontal and so as to be capable of turning, includes a pair of shaft flaw detection heads configured so as to be capable of sandwiching the crank pin therebetween, and including a first probe capable of detecting a flaw on a cylindrical surface of the crank pin or a second probe capable of detecting a flaw in a fillet section which is a coupling section between the crank pin and the web, and a perpendicular surface flaw detection head configured so as to be capable of coming in contact with the crank pin, and including a third probe capable of detecting a flaw on a side surface of the web, where the perpendicular surface flaw detection head and the pair of shaft flaw detection heads are configured to be movable on a perpendicular surface.

DESCRIPTION OF EMBODIMENTS

A detailed description is given of embodiments of a crankshaft flaw detection device according to the present invention properly referring to drawings.

First Embodiment

Figure 1:
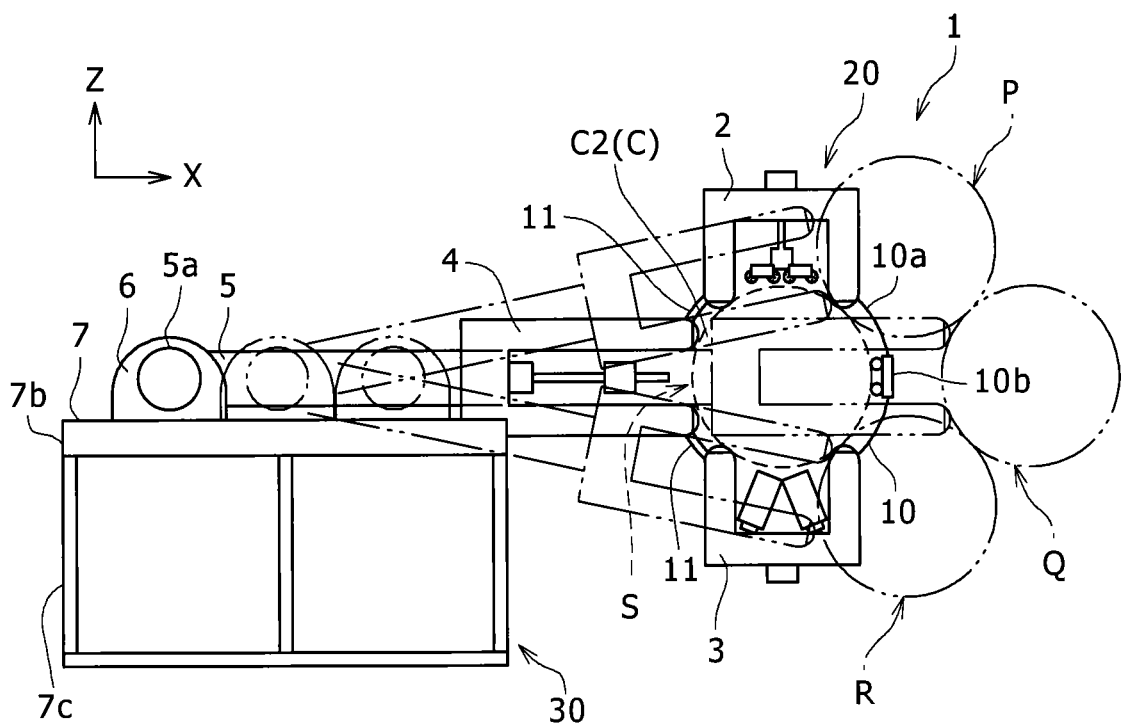
FIG. 1 is a side view schematically showing a crankshaft flaw detection device according to a first embodiment of the present invention
Figure 2:
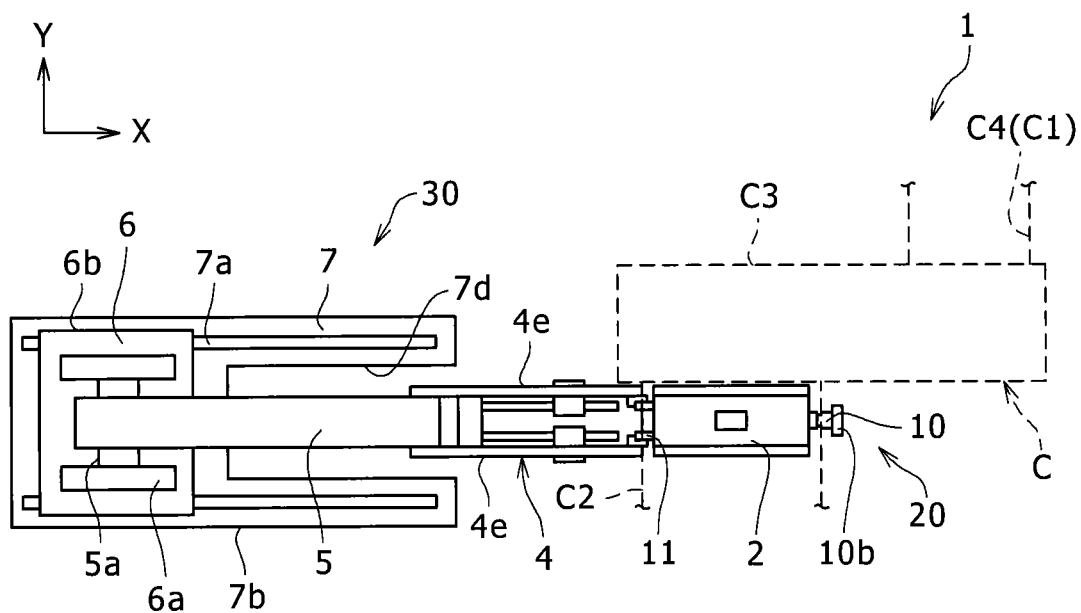
FIG. 2 is a plan view schematically showing the crankshaft flaw detection device according to the first embodiment of the present invention

The crankshaft flaw detection device according to this embodiment is a device for detecting a flaw in a crankshaft arranged horizontally. As shown in FIGS. 1 and 2, a crankshaft C includes a shaft main body C1, a crank pin C2 provided in parallel with the shaft main body C1 at an eccentric position with respect to the shaft main body C1, and webs C3 for connecting the shaft main body C1 and the crank pin C2 with each other. At least two journal sections C4 are provided on the shaft main body C1. The crank pin C2 is provided between the journal sections C4 neighboring each other.

This crankshaft flaw detection device can carry out a surface flaw detection in the crank pin C2, a side surface flaw detection in the web C3, and a flaw detection in a fillet section. Moreover, this crankshaft flaw detection device can also carry out a surface flaw detection in the journal section C4.

The crankshaft flaw detection device 1 includes a scanning unit for flaw detection 20 and a base 30 for supporting the scanning unit for flaw detection 20 in a movable manner as shown in FIG. 1. The scanning unit for flaw detection 20 includes an upper side shaft flaw detection head 2, a lower side flaw detection head 3, a perpendicular surface flaw detection head 4, and a coupling arm 5. The base 30 includes a slider 6 and a support stand 7. A specific description is now given of a structure of the crankshaft flaw detection device 1. It should be noted that a page up/down direction is referred to as Z axis direction (perpendicular direction), and a page left/right direction orthogonal to the Z axis is referred to as X axis direction in FIG. 1, FIG. 3(A), FIG. 4(A), FIG. 5(A), and FIG. 6(A) in the following description. Moreover, the page up/down direction is referred to as Y axis direction, and the page left/right direction orthogonal to the Y axis is referred to as X axis direction in FIG. 2 and FIG. 6(B). Moreover, a page up/down direction is referred to as Z axis direction, and the page left/right orthogonal to the Z axis is referred to as Y axis direction in FIG. 3(B), FIG. 4(B), and FIG. 5(B). The X axis direction is a direction orthogonal to an axial center direction of the journal sections C4, and the Y axis direction is a direction parallel with the axial center of the journal sections C4. The X axis directions, the Y axis directions, and the Z axis directions in the different figures respectively direct to the same directions.

When the crankshaft C rotates around the axial center of the journal sections C4, the crank pin C2 revolves around the axial center of the journal sections C4 as shown in FIG. 1. A state S in which the crank pin C2 is closest to the support stand 7 is shown in broken lines in FIG. 1. Moreover, a state P in which the crank pin C2 reaches the most upper position, a state Q in which the crank pin C2 reaches the farthest position from the support stand 7, a state R in which the crank pin C2 reaches the most lower position are shown in long dashed double-short dashed lines in FIG. 1 in addition to the state S. Moreover, the crankshaft flaw detection device 1 is partially (the perpendicular surface flaw detection head 4, the coupling arm 5, and the slider 6 are) represented by long dashed double-short dashed lines in these states P, Q, and R.

<Scanning Unit for Flaw Detection>

The scanning unit for flaw detection 20 includes the upper side shaft flaw detection head 2, the lower side flaw detection head 3, the perpendicular surface flaw detection head 4, and the coupling arm 5. The upper side shaft flaw detection head 2 includes first probes 2b, and a bearing part which comes in contact with the crank pin C2 approximately from above. The lower side shaft flaw detection head 3 includes second probes 3b, and a bearing part which comes in contact with the crank pin C2 approximately from below. The perpendicular surface flaw detection head 4 includes third probes 4b, and a bearing part which comes in contact with the crank pin X approximately laterally (in the X axis direction). The upper side shaft flaw detection head 2 and the lower side shaft flaw detection head 3 are respectively coupled via coupling sections 11 to the perpendicular surface flaw detection head 4. These upper side shaft flaw detection head 2, the lower side shaft flaw detection head 3, and the perpendicular surface flaw detection head 4 functions as bearings attached to the crank pin C2 while maintaining the crank pin C2 in a rotatable state.

The perpendicular surface flaw detection head 4 is coupled to the coupling arm 5 in an approximately column shape body. One end of the coupling arm 5 is connected to an end opposite to an end which comes in contact with the crank pin C2 in the perpendicular surface flaw detection head 4. The other end of the coupling arm 5 is coupled to the slider 6.

A coupling belt 10 is attached to the lower side shaft flaw detection head 3. The upper side shaft flaw detection head 2 is configured to lock an end of the coupling belt 10. The bearing parts (the upper side shaft flaw detection head 2, the lower side shaft flaw detection head 3, and the perpendicular surface flaw detection head 4) of the scanning unit for flaw detection 20 can be mounted on the crank pin C2 by locking the end of the coupling belt 10 to the upper side shaft flaw detection head 2, thereby maintaining the state in which the scanning unit for flaw detection 20 is mounted on the crank pin C2.

<Upper Side Shaft Flaw Detection Head>

Figure 3:
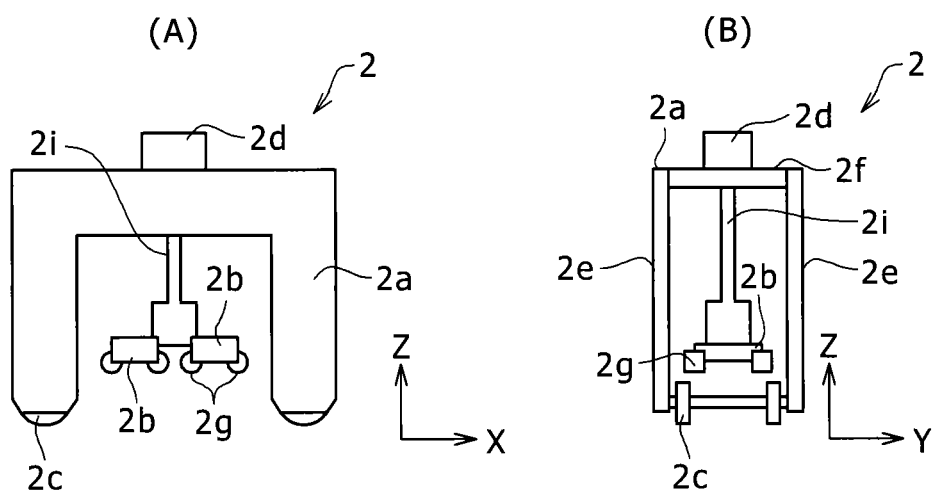
FIG. 3(A) is a side view schematically showing an upper side shaft flaw detection head provided on the crankshaft flaw detection device.
FIG. 3(B) is a schematic front view of the upper side shaft flaw detection head viewed from a right side in FIG. 1.

The upper side shaft flaw detection head 2 includes a frame 2a, two first probes 2b, wheels 2c, and a position adjustment mechanism 2d as shown in FIG. 1, FIG. 2, and FIGS. 3(A) and (B).

The frame 2a holds the first probes 2b, and includes two flat plates 2e arranged approximately parallel with each other, a flat plate 2f for connecting them with each other, and multiple connection rods (not shown). Each of the flat plate 2e forming a sidewall of the frame 2a includes a base section formed in a horizontally oblong approximately rectangular shape, and protruded sections respectively extending downward from ends in a lengthwise direction of the base section. In other words, the flat plate 2e has such a shape that the protruded sections each in an approximately rectangular shape are formed along the widthwise direction (Z axis direction) from the both ends of the base section in a side view. The flat plate 2f in an approximately rectangular shape in a plan view is connected, as a bottom wall (connection wall), to long sides in bottom sections of the two sidewalls, and the multiple connection rods (not shown) are connected to long sides on outer sides of the protruded sections. The base section and the pair of protruded sections form an internal space section in the frame 2a.

The sizes of the frame 2a are not particularly limited as long as tips of the first probes 2b can be brought close to the surface of the crank pin C2 while the first probes 2b are held. For example, a length (length of the long side of the bottom section of the flat plate 2e constructing the sidewall) of the frame 2a may be equal to or more than 70 mm, and equal to or less than 600 mm. A height of the frame 2a (height from a bottom end to a state of the flat plate 2e constructing the sidewall (distance from a short side of the protruded section to the opposing long side of the bottom section)) may be equal to or more than 100 mm and equal to or less than 300 mm. A width (distance between the sidewalls) of the frame 2a may be equal to or more than 100 mm and equal to or less than 200 mm. Moreover, thicknesses of the sidewalls (flat plates 2e) and the bottom wall (flat plate 2f) of the frame 2a may be respectively, for example, equal to or more than 3 mm, and equal to or less than 20 mm.

A material of the frame 2a is not limited as long as a strength can be maintained. For example, the material of the frame 2a may be a metal such as aluminum. Moreover, the sidewalls (flat plates 2e), the bottom wall (flat plate 2f), and the connection rods constructing the frame 2a may be connected to one another by, for example, fastening bolts and nuts (not shown).

The first probes 2b are arranged on the upper side shaft flaw detection head 2, and carry out the flaw detection on the surface (cylindrical surface) and an inside of the crank pin C2. The first probe 2b includes a probe main body for carrying out the flaw detection on the crank pin C2, and transmitting a signal, a holder for storing the probe main body, and rollers for probe 2g which come in contact with the crank pin C2. The two first probes 2b are arranged side by side in the X axis direction, and are placed side by side in a peripheral direction on an outer peripheral surface on a top section of the outer peripheral surface of the crank pin C2.

Publicly known probes for metal may be used as probes used for the first probes 2b, and, for example, ultrasonic probes may be used.

The roller for probe 2g is a roller for rolling about a shaft parallel with a rotational axis of the crankshaft C. The rollers for probe 2g are in contact with the outer peripheral surface of the crank pin C2 during the flaw detection, and rotate as the crank pin C2 rotates. The roller for probe 2g is journalled by a bearing provided on a side of the holder close to the crank pin C2. When the crankshaft C rotates in a state in which the scanning unit for flaw detection 20 is mounted on the crank pin C2, the rollers for probe 2g in contact with the crank pin C2 rotate. On this occasion, the surface of the crank pin C2 can be scanned without a displacement in position of the probe main bodies.

The first probes 2b are connected to a rod 2i of the position adjustment mechanism 2d. The rod 2i extends in the contact direction from the flat plate 2f constructing the bottom wall of the upper side shaft flaw detection head 2 to the crank pin C2. The two first probes 2b are arranged on a tip of the rod 2i.

The first probes 2b are supported so as to be displaced in the axial direction of the crank pin C2 by the position adjustment mechanism 2d. In other words, the rod 2i can swing on a plane parallel with the axial center direction of the crank pin C2, and the first probes 2b thus displace in the axial direction when the rod 2i swings.

The wheel 2c is a cylindrical body for rotation about a shaft parallel with the rotational axis of the crankshaft C. The wheel 2c is in contact with the crank pin C2 in a rotational state. In other words, the wheel 2c functions as a rolling element of a rolling bearing. The wheel 2c is provided on the end of each of the protruded sections of the each sidewall of the frame 2a. The upper side shaft flaw detection head 2 includes a total of four wheels 2c each provided on the each protruded section of the frame 2a. The shaft of the wheel 2c is inserted through each of the wheels 2c. The upper side shaft flaw detection head 2 is in contact with the crank pin C2 via the wheels 2c, and the frame 2a does not rotate along with the rotation of the crank pin C2. Thus, the attitude of the frame 2a can be maintained during the scan. It should be noted that the wheels 2c may be arranged inside or outside the frame 2a.

Sizes of the wheels 2c are not particularly limited. For example, a diameter of the wheels 2c may be equal to or more than 10 mm, and equal to or less than 100 mm. Moreover, a width of the wheels 2c may be equal to or more than 10 mm, and equal to or less than 60 mm. Moreover, a material of the wheels 2c is not particularly limited. For example, the material of the wheels 2c may be the stainless steel.

The position adjustment mechanism 2d is a mechanism for adjusting the position of the first probes 2b. The position adjustment mechanism 2d has a function of changing the position of the first probes 2b in the radial direction (Z axis direction) of the crank pin C2, and a function of changing the position of the first probes 2b in the axial direction (Y axis direction) of the crank pin C2.

A displacement mechanism by means of a thread may be employed as the mechanism for changing the Z axis direction position of the first probes 2b. The rod 2i configured so that thread grooves or thread ridges are formed on a column body is used, and the rod 2i is connected to the first probes 2b, for example, as shown in FIG. 3(A). A rotor (not shown) threadedly engaging with the thread grooves or thread ridges of the rod 2i is held for rotation by the flat plate 2f (bottom wall). Then, the rod 2i can be moved in the Z axis direction by rotating the rotor.

Moreover, a mechanism for turning or swinging the rod 2i in the peripheral direction of the crank pin C2 about a fulcrum which is one point of the rod 2i, for example, may be used as the mechanism for changing (swinging) the Y axis direction position of the first probes 2b. For example, actuators, manual winches, or the like may be used as power sources for these mechanisms.

The crankshaft flaw detection device 1 can carry out the flaw detection for various crankshafts C different in the diameter by enabling adjustment of the position of the first probes 2b in the radial direction of the crank pin C2. Moreover, a possible flaw detection area in the axial direction of the crank pin C2 can be increased by enabling adjustment of the position of the first probes 2b in the axial direction of the crank pin C2. Thus, a flaw detection operation efficiency by the crankshaft flaw detection device 1 can be increased.

<Lower Side Shaft Flaw Detection Head>

Figure 4:
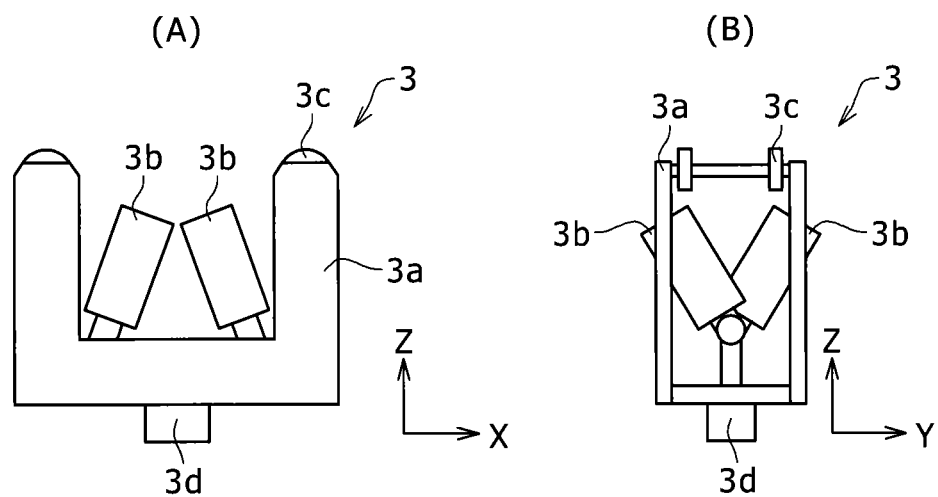
FIG. 4(A) is a side view schematically showing a lower side shaft flaw detection head provided on the crankshaft flaw detection device.
FIG. 4(B) is a schematic front view of the lower side shaft flaw detection head viewed from the right side in FIG. 1.

The lower side shaft flaw detection head 3 includes a frame 3a, the two second probes 3b, wheels 3c, and a position adjustment mechanism 3d as shown in FIG. 1, FIG. 2, and FIGS. 4(A) and (B). The frame 3a has approximately the same shape as of the frame 2a of the upper side shaft flaw detection head 2, and the sizes and the material may be the same as the sizes and the material of the frame 2a of the upper side shaft flaw detection head 2. Moreover, the wheels 3c are configured as the wheels 2c of the upper side shaft flaw detection head 2.

The second probes 3b are arranged inside the lower shaft flaw detection head 3, and carry out the flaw detection on fillet sections (joint sections between the crank pin C2 and the webs C3). Publicly known probes for metal may be used as probes used for the second probes 3b, and, for example, ultrasonic probes may be used. Further, the flaw detection is preferably carried out while the fillet sections are in an immersed state from the viewpoint of an increase in the precision. A method of covering tips of the probe 3b and the fillet section subject to the flaw detection with a cover, and injecting water in the cover, for example, may be mentioned as a method of bringing the fillet sections in the immersed state. Moreover, a probe of the phased array type capable of dividing the fillet section into multiple zones, thereby easily and surely carrying out the flaw detection is preferably used as the probe used as the second probe 3b.

The two second probes 3b are arranged so as to be tilted in the circumferential direction (X axis direction) of the crank pin C2 so that the flaw detection direction orients toward the center (axial center) of the crank pin C2 as shown in FIG. 4(A). Moreover, the two second probes 3b are arranged so as to be tilted in the directions of line symmetry (one is toward a plus side of the Y axis direction, and the other is toward a minus side of the Y axis direction) in the axial direction (Y axis direction) of the crank pin C2 as shown in FIG. 4(B). A reason for the tilted arrangement of the second probes 3b in this way is to easily and surely carry out the scanning for flaw detection on the fillet sections. Moreover, a reason for arranging the two second probes 3b line-symmetrically in the axial direction of the crank pin C2 is to carry out the scanning for flaw detection on the fillet sections without changing the direction of the crankshaft flaw detection device 1 on the both end sides of the crank pin C2. The number of the second probes 3b included in the lower side shaft flaw detection head 3 may be one. If one second probe 3b is provided, after the flaw detection on the one fillet section, the scanning for flaw detection can be carried out on the other fillet section by changing a tilted angle of the second probe 3b in the axial direction (Y axis direction) of the crank pin C2 to an opposite direction.

The position adjustment mechanism 3d is configured so as to be able to change the attitudes of the second probes 3b so that the fillet section is included in a flaw detection area subject to the flaw detection while the two second probes 3b are held. The position adjustment mechanism 3d can change the tilted angle in the Y axis direction and the height (position in the Z axis direction) of each of the second probes 3b. A mechanism for rotating the second probes 3b by using actuators, manual winches, or the like, a mechanism for moving rods to which the second probes 3b are connected, or the like may be used in the same way as the position adjustment mechanism 2d of the upper side shaft flaw detection head 2, for example, as the position adjustment mechanism 3d.

The flaw detection by using the crankshaft flaw detection device 1 can be carried out for various crankshafts C different in the diameter by enabling the change in the tilted angle and the height of the second probes 3b.

<Perpendicular Surface Flaw Detection Head>

Figure 5:
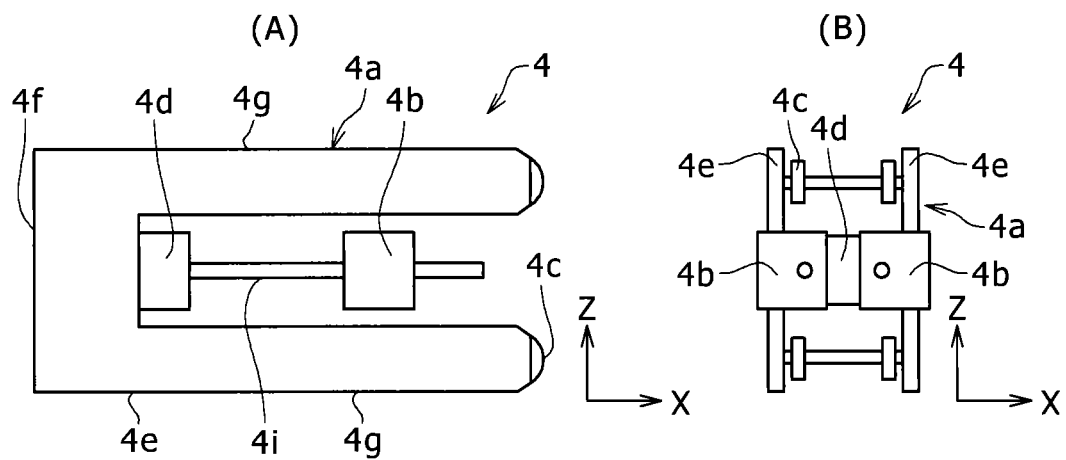
FIG. 5(A) is a side view schematically showing a perpendicular surface flaw detection head provided on the crankshaft flaw detection device.
FIG. 5(B) is a schematic front view of the perpendicular surface flaw detection head viewed from the right side in FIG. 1.

The perpendicular surface flaw detection head 4 includes a frame 4a, the two third probes 4b, wheels 4c, and a position adjustment mechanism 4d as shown in FIG. 1, FIG. 2, and FIGS. 5(A) and (B). The frame 4a is formed by two flat plates 4e arranged approximately parallel with each other, and a flat plate, which is not shown, for connecting the flat plates 4e with each other. Each of the flat plate 4e forming sidewalls of the frame 4a includes a base section 4f formed in a vertically oblong approximately rectangular shape, and protruded sections 4g respectively extending laterally from both ends in a lengthwise direction of the base section 4f. In other words, the flat plate 4e has such a shape that the protruded sections 4g each in an approximately rectangular shape are formed along the widthwise direction (x axis direction) from the both top/bottom ends of the base section 4f in a side view. A plate approximately in a rectangular shape in a plan view is connected as a bottom wall to long sides of the base sections 4f of the two sidewalls, which forms the frame 4a having an internal space section. It should be noted that the wheels 4c are the same as the wheels 2c of the upper side shaft flaw detection head 2.

The sizes of the frame 4a are not particularly limited as long as a movable range of the third probes 4b capable of carrying out the scanning for flaw detection on the side surfaces of the webs C3 can be secured. For example, the length (length of the long sides of the bottom sections of the sidewalls) of the frame 4a may be equal to or more than 100 mm, and equal to or less than 1000 mm. A width (distance between the sidewalls) of the frame 4a may be equal to or more than 100 mm and equal to or less than 400 mm. Moreover, thicknesses of the sidewalls (flat plates 4e) and the bottom wall of the frame 4a may be respectively, for example, equal to or more than 3 mm, and equal to or less than 20 mm.

The third probes 4b are respectively arranged on both wall surface sides of the perpendicular surface flaw detection head 4 so as to carry out the scanning for flaw detection on the side surfaces of the webs C3 on both left and right sides of the frame 4a. It should be noted that the side surface of the web C3 on which the third probe 4b carries out the scanning for flaw detection is a surface which is orthogonal to the axial center of the crank pin C2, and from which the crank pin C2 protrudes out of surfaces of the web C3. The third probe 4b is arranged on a sidewall surface side so as to be included between the protruded sections 4g of the flat plate 4e constructing the sidewall of the frame 4a. The scanning for flaw detection can be carried out on the respective side surfaces of the webs C3 on the both ends of the crank pin C2 without changing the direction of the crankshaft flaw detection device 1 by arranging the third probes 4b on the both sidewall sides in this way. Publicly known probes for metal may be used as probes used for the third probes 4b, and, for example, ultrasonic probes may be used.

The third probes 4b are coupled to the position adjustment mechanism 4d, and are configured to reciprocally move toward the crank pin C2 with which the perpendicular surface flaw detection head 4 comes in contact.

The position adjustment mechanism 4d is a mechanism coupled to the third probes 4b for changing the position of the third probes 4b in the radial direction (X axis direction) of the crank pin C2. A displacement mechanism by means of a thread may be employed as the position adjustment mechanism 4d. For example as shown in FIGS. 5(A) and (B), a rod 4i on which a thread is formed passes through the third probes 4b, and a mechanism for rotating the rod 4i by means of an actuator, a manual winch, or the like can be used as the position adjustment mechanism 4d.

The position in the X axis direction of the third probes 4b can be changed as the crank shaft C rotates by enabling the change in the position in the X axis direction of the third probes 4b. Thus, the side surfaces of the webs C3 extending in the radial direction of the crank pin C2 can be scanned by the third probes 4b.

<Other Flaw Detection Constructed Components>

The coupling arm 5 is approximately a quadrangular prism, one end thereof is connected to the frame 4a of the perpendicular surface flaw detection head 4, and the other end is coupled to the slider 6 for rotation about the slider 6. Specifically, the one end of the coupling arm 5 is connected by means of, for example, fastening of bolts and nuts, to the base section 4f of the sidewalls forming the frame 4a of the perpendicular surface flaw detection head 4. Moreover, the coupling arm 5 includes a shaft 5a extending in the direction parallel with the axial direction (Y axis direction) of the crank pin C2 at the other end. The shaft 5a passes through slider bearings 6a included in the slider 6 described later. Then, the coupling arm 5 is journalled by the slider 6 at the other end thereof.

Sizes of the coupling arm 5 are not particularly limited as long as the coupling arm 5 is strong enough to support the upper side shaft flaw detection head 2, the lower side shaft flaw detection head 3, and the perpendicular surface flaw detection head 4, and is long enough to follow the revolution of the crank pin C2 as the crankshaft C rotates. It should be noted that the coupling arm 5 may be hollow.

A material of the coupling arm 5 is not particularly limited, and, for example, carbon steel may be used.

The coupling sections 11 are members for coupling the upper side shaft flaw detection head 2 and the lower side shaft flaw detection head 3 to the perpendicular surface flaw detection head 4. Specifically, the coupling section 11 is a thick plate in an approximately rectangular shape in a plan view, and includes bearings on both ends. The shaft for the wheels 2c included by the upper side shaft flaw detection head 2 is inserted into the one bearing, and a shaft for the wheels 4c included in the perpendicular surface flaw detection head 4 is inserted into the other bearing. As a result, the upper side shaft flaw detection head 2 and the perpendicular surface flaw detection head 4 are coupled to each other by the coupling section 11. In other words, the upper side shaft flaw detection head 2 is coupled via the coupling section 11 to the perpendicular surface flaw detection head 4 so as to change the direction with respect to the perpendicular surface flaw detection head 4 on a perpendicular surface. Moreover, the lower side shaft flaw detection head 3 and the perpendicular surface flaw detection head 4 are coupled to each other by means of the same method. In other words, the lower side shaft flaw detection head 3 is coupled via the coupling section 11 to the perpendicular surface flaw detection head 4 so as to change the direction with respect to the perpendicular surface flaw detection head 4 on a perpendicular surface.

If the upper side shaft flaw detection head 2, the lower side shaft flaw detection head 3, and the perpendicular surface flaw detection head 4 are coupled to one another by the coupling sections 11 in this way, angles formed by the perpendicular surface flaw detection head 4, the upper side shaft flaw detection head 2, and the lower side shaft flaw detection head 3 can be freely adjusted.

Therefore, a change in the diameter of the crank pin C2 can be easily and surely adapted.

It should be noted that the coupling section 11 for coupling the upper side shaft flaw detection head 2 and the perpendicular surface flaw detection head 4 to each other is not limited to the configuration enabling the adjustment of the angle through the insertions of the shafts of the wheels 2c and 4c. For example, it is possible to employ such a configuration that shafts independent of the shafts for the wheels 2c and 4c are provided on the flaw detection heads 2 and 4, and the shafts are inserted into the coupling section 11. Moreover, it is possible to employ such a configuration that shafts are provided on both ends of the coupling section 11, and are inserted into holes formed on the frames 2a and 4a of the flaw detection heads 2 and 4. The same holds true for the coupling section 11 for coupling the lower side shaft flaw detection head 3 and the perpendicular surface flaw detection head 4 to each other.

Sizes of the coupling sections 11 are not particularly limited. For example, a length of the coupling section 11 may be equal to or more than 10 mm, and equal to or less than 200 mm. Moreover, a width of the coupling section 11 may be equal to or more than 10 mm, and equal to or less than 100 mm. Moreover, a thickness of the coupling section 11 may be equal to or more than 3 mm, and equal to or less than 20 mm. Moreover, the coupling section 11 preferably includes a cut out in a trapezoidal shape on a side close to the crank pin C2 in order to avoid a contact with the crank pin C2.

The coupling belt 10 is a member for coupling the upper side shaft flaw detection head 2 and the lower side shaft flaw detection head 3 to each other, and is constructed by an elastic body. One end of the coupling belt 10 is fixed to the protruded section of the frame 3a of the lower side shaft flaw detection head 3 on a side opposite to the perpendicular surface flaw detection head 4. A hook 10a is attached to the other end of the coupling belt 10. The coupling belt 10 includes a belt cart 10b at a center section. The hook 10a is suspended on the frame 2a of the upper side shaft flaw detection head 2 when the scanning unit for flaw detection 20 is mounted on the crank C2.

The belt cart 10b includes an adjuster for adjusting the length of the coupling belt 10, and a plurality of wheels in rotationally contact with the surface of the crank pin C2. A publicly known adjuster may be used as the adjuster. For example, such a type that the coupling belt 10 is inserted between a lever section and a base section, and the coupling belt 10 is locked by pushing down the lever section may be used as the adjuster.

The length of the coupling belt 10 can be adjusted by the belt cart 10b depending on the diameter of the crank pin C2, and the scanning unit for flaw detection 20 can thus be easily and surely mounted on the crank pin C2. Moreover, the belt cart 10b comes in contact with the crank pin C2 via the wheels, and the coupling belt 10 can thus be prevented from coming in direct contact with the crank pin C2, and thus presenting a sliding motion.

A material of the coupling belt 10 is not particularly limited as long as the material is an elastic body, and, for example, nylon may be used.

<Base>

Figure 6:
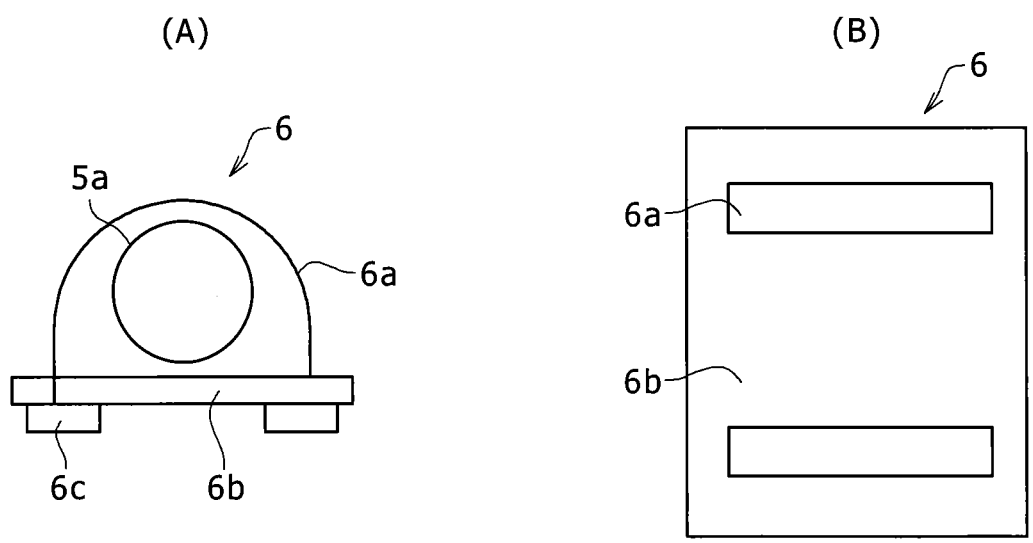
FIG. 6(A) is a side view schematically showing a slider provided on the crankshaft flaw detection device.
FIG. 6(B) is a plan view schematically showing the slider.

The base 30 includes a slider 6 and a support stand 7. The slider 6 includes two slider bearings 6a and the slider base plate 6b as shown in FIG. 1, FIG. 2, and FIGS. 6(A) and (B). The slider bearings 6a are sections for journaling the shaft 5a included by the coupling arm 5 on the both sides, and are arranged on a front surface (a top surface facing a positive direction side of the Z axis) side of the slider base plate 6b. The two slider bearings 6a are arranged with each other. A total of four rail rollers 6c are arranged as two rows in the X axis direction, and two rows in the Y axis direction on a rear surface side of the slider base plate 6b. The rail rollers 6c roll along rails 7a for slider included by the support stand 7. The slider 6 is configured to be movable in the horizontal direction (X axis direction) along the rails 7a for slider.

Sizes of the slider base plate 6b are not particularly limited. Moreover, carbon steel, for example, may be used as a material for the slider bearings 6a, the slider base plate 6b, and the rail rollers 6c.

The support stand 7 is a stand for supporting the scanning unit for flaw detection 20 and the slider 6, and is constructed by a top plate 7b and multiple pillars 7c vertically connected to the top plate 7b. The support stand 7 includes the rails 7a for slider on which the rail rollers 6c of the slider 6 can travel in the direction (X axis direction) vertical to the axial center of the crankshaft C on the front surface (surface on the positive direction side of the Z axis) of the top plate 7b.

The top plate 7b of the support stand 7 includes a cutout section 7d in a rectangular shape on the crank pin C2 side. The cutout section 7d is shaped so that tips (upper side shaft flaw detection head 2, lower side shaft flaw detection head 3, perpendicular surface flaw detection head 4, and coupling arm 5) of the scanning unit for flaw detection 20 mounted on the crank pin C2 can move to a position lower than the top plate 7b. A width (Y axis direction) of the cut out section 7d is more than widths of the horizontal surface flaw detection head 4 and the coupling arm 5. Even when the crank pin C2 moves to a position lower than the top plate 7b as a result of the rotation of the crankshaft C, the cutout section 7d enables the scanning unit for flaw detection 20 to move following the crank pin C2.

Moreover, the support stand 7 is configured so as to be movable on a perpendicular surface (Y-Z plane) parallel with the journal sections, which is not shown. This configuration can be constructed by parallel movement means capable of moving the support stand 7 approximately parallel with the journal sections and perpendicular movement means capable of moving the support stand 7 in the perpendicular direction, for example. Means constructed by wheels attached to the pillar sections of the support stand 7 and rails engaging with the wheels, for example, may be mentioned as the movement means. Moreover, means for using a jack or the like to change the length of the pillars of the support stand 7, for example, may be mentioned as the perpendicular movement means.

The sizes of the support stand 7 are not particularly limited as long as a movable range capable of pulling out the perpendicular surface flaw detection head 4 from the side surfaces of the webs C3 can be secured. For example, a length (X axis direction) of the support stand 7 may be equal to or more than 100 mm, and equal to or less than 2000 mm. Moreover, a width (Y axis direction) of the support stand 7 may be equal to or more than 100 mm and equal to or less than 1000 mm. Moreover, a height (Z axis direction) of the support stand 7 may be equal to or more than 500 mm and equal to or less than 1500 mm. Moreover, as the sizes of the cutout section 7d, for example, a length may be equal to more than 100 mm and equal to or more than 1500 mm, and a width may be equal to more than 100 mm and equal to or less than 800 mm. Further, as the sizes of the rail for slider 7a, for example, a length may be equal to more than 100 mm and equal to or less than 1500 mm, and a width may be equal to more than 5 mm and equal to or less than 50 mm.

<Method of Using Crankshaft Flaw Detection Device (Scanning Method for Flaw Detection of Crankshaft)>

A description is now given of a flaw detection method for the crankshaft C by using the crankshaft flaw detection device 1.

First, the crankshaft flaw detection device 1 is arranged on a side (X axis direction) of the crank pin C2 of the crankshaft C subject to the flaw detection. More specifically, the flaw detection device 1 is arranged at such a position that the flaw detection heads 2, 3, and 4 are close to the webs C3 when the scanning unit for flaw detection 20 is mounted on the crank pin C2. On this occasion, the pillars of the support stand 7 are preferably fixed to a floor surface by means of anchoring or the like from the viewpoint of precision and safety.

The position of the flaw detection device 1 is adjusted so that the wheels 4c of the perpendicular flaw detection head 4 are in contact with the surface of the crank pin C2. On this occasion, if the crankshaft C is rotated so that the center of the crank pin C2 is as high as the axial center of the crankshaft C, an operation of mounting the scanning unit for flaw detection 20 can be easily carried out.

After the wheels 4c of the perpendicular surface flaw detection head 4 are laterally brought in contact with the surface of the crank pin C2, the upper side shaft flaw detection head 2 is turned about the coupling section 11 as a fulcrum so that the wheels 2c of the upper side shaft flaw detection head 2 come in contact with the surface of the crank pin C2.

After the wheels 2c of the upper side shaft flaw detection head 2 are brought in contact with the surface of the crank pin C2 from above, the lower side shaft flaw detection head 3 is turned about the coupling section 11 as a fulcrum so that the lower side shaft flaw detection head 3 is close to the crank pin C2, and the wheels 3c of the lower side shaft flaw detection head 3 come in contact with the surface of the crank pin C2 from below.

After the operation of bringing the lower side shaft flaw detection head 3 in contact with the crank pin C2, the hook 10a of the coupling belt 10 is suspended from the frame 2a of the upper side shaft flaw detection head 2. After the suspension of the hook 10a, a suspended length of the coupling belt 10 is decreased by using the adjuster of the belt cart 10b, thereby bringing the wheels 3c of the lower side shaft flaw detection head 3 in contact with the surface of the crank pin C2. As a result, the scanning unit for flaw detection 20 is mounted on the crank pin C2.

After the scanning unit for flaw detection 20 is mounted on the crank pin C2, the scanning unit for flaw detection 20 adjusts positions in the radial direction of the first probes 2b included by the upper side shaft flaw detection head 2. Similarly, the scanning unit for flaw detection 20 adjusts positions in the radial direction and tilting angles in the axial direction of the second probes 3b of the lower shaft flaw detection head 3.

After the position adjustment of each of the probes is finished, each of the probes is activated, and the crankshaft C is rotated. When the crankshaft C is rotated, the crank pin C2 revolves about the journal sections C4 as shown by the long dashed double-short dashed lines in FIG. 1. The scanning unit for flaw detection 20 of the crankshaft flaw detection device 1 is configured to be movable on the perpendicular surface vertical to the axial center of the crankshaft C (journal section C4), and is also in contact with the crank pin C2 via the roller bearings, which are the rotatable multiple wheels 2c, 3c, and 4c serving as rolling elements. As a result, the tips themselves of the flaw detection heads 2, 3, and 4 mounted on the crank pin C2 do not rotate, but follow the revolution of the crank pin C2 as illustrated by the long dashed double-short dashed lines in FIG. 1 through the movements of the flaw detection heads 2, 3, and 4 caused by the horizontal movement of the slider 6 and the swing of the coupling arm 5 about the shaft 5a. As a result, the surface of the crank pin C2 relatively moves in the peripheral direction with respect to the flaw detection heads 2, 3, and 4. On this occasion, when the crankshaft C is rotated by one turn, the surface of the crank pin C2 also rotates by one turn relatively to the flaw detection heads 2, 3, and 4, and the web C3, the crank pin C2, and the fillet section can be scanned while the third probe 4b is directed to the side surface of the web C3, the first probes 2b are directed to the surface of the crank pin C2, and the second probe 3b is directed to the fillet section.

When the crankshaft C is rotated, the positions of the first probes 2b of the upper side shaft flaw detection head 2 are changed (swung) in the axial direction (Y axis direction) each time the crankshaft C rotates by one turn. As a result, the scanning for flaw detection can be carried out on the crank pin C2 to a wide extent in the axial direction. The change in the positions of the first probes 2b may be manual or automatic, however is preferably automatic from the viewpoint of efficiency. Moreover, the positions of the third probes 4b of the perpendicular surface flaw detection head 4 are adjusted in the radial direction in accordance with the rotation of the crankshaft C so as to scan the side surface of the web Y. The adjustment of the positions of the third probes 4b may be automatic or manual, however is preferably automatic from the view point of efficiency and from the view point of the scan on the side surface of the web C3 without omission.

The scanning for flaw detections on the crank pin C2, the fillet section, and the side surface on the crank pin C2 side of the web C3 can be carried out simultaneously by adjusting the positions of the respective probes by using the first probes 2b of the upper side shaft flaw detection head 2, the second probe 3b of the lower side shaft flaw detection head 3, and the third probe 4b of the perpendicular surface flaw detection head 4 as the crankshaft rotates as described above. It should be noted that, out of the two second probes 3b included by the lower side shaft flaw detection head 3 and the two third probes 4b included by the perpendicular surface flaw detection head 4, only the probes on the side close to the web C3 are used, and the flaw detections by using the other probes are not carried out.

When the scanning for flaw detection for a applicable scanning area at the position at which the scanning unit for flaw detection 20 is mounted is finished, the scanning unit for flaw detection 20 is removed from the crank pin C2. Then, the crankshaft flaw detection device 1 is moved in the axial direction of the crank pin C2, and the scanning unit for flaw detection 20 is mounted on a section where the scanning for flaw detection has not been carried out by following the sequence described above. Then, the scanning for flaw detection is carried out in the area where the scanning for flaw detection can be carried out while the crankshaft C is rotated. The scanning for flaw detection can be carried out on the entire crank pin C2 by repeating this operation. It should be noted that when the web C3 on the side opposite to the web C3 on which the scanning for flaw detection is carried out first is reached, the scanning for flaw detections can be carried out on the side surface and the fillet section of the web C3 on the opposite side by switching the second probe 3b of the lower side shaft flaw detection head 3 and the third probe 4b used by the perpendicular surface flaw detection head 4 to the probes on the opposite side.

The crankshaft flaw detection device 1 mounts the scanning unit for flaw detection 20 on the crank pin C2 of the crankshaft C, and can follow the revolution of the crank pin C2 generated by the rotation of the crankshaft C in this way. Therefore, the scanning for flaw detections on the crank pin C2, the side surfaces of the webs C3, and that of the fillet sections can be automated. As a result, a period and a cost required for the flaw detection on the crankshaft C can be greatly reduced.

The crankshaft flaw detection device 1 can also mount the scanning unit for flaw detection 20 on the journal section C4.

Specifically, the upper side shaft flaw detection head 2 and the lower side shaft flaw detection head 3 of the scanning unit for flaw detection 20 can sandwich the journal section C4. When the crankshaft C is rotated in this state, the scanning for flaw detection on a surface (cylindrical surface) of the journal section C4 can be carried out by using the first probes 2b, the scanning for flaw detection on joint sections between the webs C3 and the journal section C4 can be carried out by using the second probes 3b, and the scanning for flaw detection on the side surfaces of the webs C3 on the journal section side (surfaces from which the journal C4 protrudes) can be carried out by using the third probes 4b.

Moreover, the crankshaft flaw detection device 1 can be preferably used for a scanning for flaw detection on a monolithic crankshaft including the journal sections C4, the crank pin C2, and the webs C3. Moreover, the crankshaft flaw detection device 1 can be preferably used for a scanning for flaw detection on an assembled crankshaft after assembly.

When the crankshaft flaw detection device 1 was used to carry out the scanning for flaw detection on the monolithic crankshaft C, a man-hour can be reduced by approximately 80% compared with a manual scanning for flaw detection.

<Other Embodiments>

The crankshaft flaw detection device according to the present invention is not limited to the embodiment. The three types of probes ranging from the first probes 2b to the third probes 4b are used in the embodiment. However, the crankshaft flaw detection device is not limited to this form, and may include four or more types of probes, for example. Moreover, for example, multiple types of probes may be arranged on the upper side shaft flaw detection head 2. The lower side shaft flaw detection head 3 does not always need to include probes in this case. Moreover, the arrangement of the probes for carrying out the flaw detections on the crank pin C2 and the fillet sections is not limited to the embodiment. For example, the first probes 2b for measuring the crank pin C2 may be arranged on the lower side shaft flaw detection head 3. In this case, probes may not be provided on the upper side shaft flaw detection head 2. Moreover, the number of each of the probes may be single.

Moreover, the embodiment uses the mechanism for coupling the scanning unit for flaw detection 20 to the base 30 for the rotational motion in order to move the upper side shaft flaw detection head 2, the lower side shaft flaw detection head 3, and the perpendicular surface flaw detection head 4 of the scanning unit for flaw detection 20 on the perpendicular surfaces. Alternatively, a mechanism enabling an up/down (perpendicular direction) reciprocal motion may be used. Such a mechanism that a rail extending in the perpendicular direction, and a slider traveling on the rail can be mentioned as the mechanism enabling the up/down reciprocal motion.

Further, though the scanning unit for flaw detection 20 is mounted via the wheels serving as the roller bearings on the crank pin C2, the bearing included by the scanning unit for flaw detection 20 are not limited to the roller bearings. For example, slide bearings, magnetic bearings, liquid bearings, and the like may be used.

Moreover, the slider 6 may be configured so as to move not in the horizontal direction but in the up/down direction (gravity direction). For example, if a rail or the like capable of moving the slider 6 in the up/down direction is provided above the crankshaft C, and the scanning unit for flaw detection 20 is arranged so as to be suspended from the slider 6, the same effects as of the embodiment can be provided.

A brief description is now given of the embodiment.

(1) The crankshaft flaw detection device includes the perpendicular surface flaw detection head to come in contact with the crank pin and the pair of shaft flaw detection heads for sandwiching the crank pin, and these flaw detection heads are configured to be movable on the predetermined perpendicular surfaces. When the crankshaft is rotated, the crank pin revolves around the axial center (rotational axis) of the journal sections of the crankshaft. On this occasion, the perpendicular surface flaw detection head and the pair of shaft flaw detection heads follow the revolution of the crank pin. Thus, when the crankshaft is rotated, the scanning for flaw detections can be carried out while the surface of the crank pin, the side surfaces of the webs, and the fillet sections are automatically followed by the respective probes. It should be noted that the pair of shaft flaw detection heads can sandwich the journal section, and the perpendicular flaw detection head can come in contact with the journal section. When the journal section of the crankshaft is sandwiched by the pair of the shaft flaw detection head and the perpendicular flaw detection head is brought in contact with the journal section in this way, the scanning for flaw detection on the journal section can be carried out by the shaft flaw detection head.

(2) Preferably, the perpendicular surface flaw detection head includes the base for supporting the perpendicular surface flaw detection head so that the perpendicular surface flaw detection head moves on the perpendicular surface orthogonal to the axial center of the journal sections, and the pair of shaft flaw detection heads are coupled to the perpendicular surface flaw detection head. Movable areas of the perpendicular surface flaw detection head and the shaft flaw detection heads can be easily adjusted depending on the sizes of the crankshaft by providing the this base. Moreover, the flaw detection heads can move on the surfaces orthogonal to the axial center of the journal sections, and can precisely scan in the peripheral direction of the outer peripheral surface of the crank pin when the crank pin revolves. Moreover, the perpendicular surface flaw detection head and the shaft flaw detection heads are coupled to one another, and the common mechanism can thus be used to move these heads, resulting in saving in space.

(3) The first probe of the pair of the shaft flaw detection heads is preferably configured to be capable of displacing in the axial direction of the crank pin sandwiched by the pair of shaft flaw detection heads. The scanning for flaw detection can automatically be carried out in a certain range of the surface in the axial direction of the crank pin (or the journal section) by configuring the first probe in this way, and a flaw detection efficiency can be increased.

(4) The second probe of the pair of shaft flaw detection heads is preferably configured to be able to carry out scanning for ultrasonic flaw detection on the fillet section in an immersed state. The flaw detection can easily and surely be carried out on the fillet section by configuring the second probe in this way.

(5) The third probe of the perpendicular surface flaw detection head is preferably configured so as to be capable of reciprocating toward the crank pin with which the perpendicular surface flaw detection head is in contact. The scanning for flaw detection can easily and surely be carried out on the side surface of the web by configuring the third probe in this way.

(6) Preferably, the upper shaft flaw detection head includes the first probe and the lower shaft flaw detection head includes the second probe. The water used for the underwater flaw detection by the second probe is prevented from being attached to the first probe and other members by arranging the first probe and the second probe in this way.

As described above, the crankshaft flaw detection device according to this embodiment can automate the flaw detections on the crank pin, the journal, the web, and the fillet section, thereby greatly decreasing the scanning time for flaw detection, and can thus be preferably used particularly for inspection of a crankshaft large in sizes.

INDUSTRIAL APPLICABILITY

The crankshaft flaw detection device according to the present invention can greatly reduce the scanning time for flaw detection on the crank pin, the journal section, the web, and the fillet section as described above. When the crankshaft flaw detection device according to the present invention is used for a large crankshaft, the cost can be greatly reduced.

EXPLANATION OF REFERENCE NUMERALS

1 Crankshaft flaw detection device
2 Upper side shaft flaw detection head
2a Frame
2b First probe
2c Wheel
2d Position adjustment mechanism
3 Lower side shaft flaw detection head
3a Frame
3b Second probe
3c Wheel
3d Position adjustment mechanism
4 Perpendicular surface flaw detection head
4a Frame
4b Third probe
4c Wheel
4d Position adjustment mechanism
5 Coupling arm
6 Slider
6a Slider bearing
6b Slider base plate
6c Rail roller
7 Support stand
7a Rail
10 Coupling belt
10a Hook
10b Belt cart
11 Coupling section
20 Scanning unit for flaw detection
30 Base

The invention claimed is:

1. A crankshaft flaw detection device for scanning for a flaw detection of a crankshaft including at least two journal sections arranged on the same axial center, a crank pin arranged in an eccentric state between the two journal sections adjacent to each other, and a web in a plate shape for coupling the crank pin and the journal section adjacent to each other, in a state where the journal sections are disposed so as to be approximately horizontal and so as to be capable of turning, comprising:
 a pair of shaft flaw detection heads configured so as to be capable of sandwiching the crank pin therebetween, and comprising a first probe capable of scanning for a flaw detection in a cylindrical surface of the crank pin or a second probe capable of scanning for a flaw detection in a fillet section which is a coupling section between the crank pin and the web; and
 a perpendicular surface flaw detection head configured so as to be capable of coming in contact with the crank pin, and comprising a third probe capable of scanning for a flaw detection in a side surface of the web orthogonal to an axial center of the crank pin,
 wherein the perpendicular surface flaw detection head and the pair of shaft flaw detection heads are configured to be movable on a predetermined perpendicular surface.

2. The crankshaft flaw detection device according to claim 1, wherein:
 the crankshaft flaw detection device comprises a base for supporting the perpendicular surface flaw detection head so that the perpendicular surface flaw detection head moves freely on a perpendicular surface orthogonal to the axial center of the journal sections; and
 the pair of shaft flaw detection heads are coupled to the perpendicular surface flaw detection head.

3. The crankshaft flaw detection device according to claim 1, wherein the first probe of the pair of the shaft flaw detection heads is configured to be capable of displacing in an axial direction of the crank pin sandwiched by the pair of shaft flaw detection heads.

4. The crankshaft flaw detection device according to claim 1, wherein the second probe of the pair of shaft flaw detection heads is configured to be able to carry out scanning for ultrasonic flaw detection on the fillet section in an immersed state.

5. The crankshaft flaw detection device according to claim 1, wherein the third probe of the perpendicular surface flaw detection head is configured so as to be capable of reciprocating toward the crank pin with which the perpendicular surface flaw detection head is in contact.

6. A crankshaft flaw detection device according to claim 4, wherein an upper shaft flaw detection head comprises the first probe and a lower shaft flaw detection head comprises the second probe.

* * * * *